United States Patent [19]

Howard et al.

[11] Patent Number: 5,089,409

[45] Date of Patent: Feb. 18, 1992

[54] METHOD OF INCREASING SPECIFIC ACTIVITY OF T-PA

[75] Inventors: Susan C. Howard, Fenton; Joseph K. Welply, St. Peters; Arthur J. Wittwer, Ellisville, all of Mo.

[73] Assignee: Monsanto Company, St. Louis, Mo.

[21] Appl. No.: 413,806

[22] Filed: Sep. 28, 1989

[51] Int. Cl.$^5$ .................. C12N 5/06; C12N 15/58; C12N 9/48
[52] U.S. Cl. ................... 435/240.2; 435/219; 435/226; 435/212
[58] Field of Search ............ 435/212, 219, 226, 240.2

[56] References Cited

U.S. PATENT DOCUMENTS

| | | | |
|---|---|---|---|
| 4,659,659 | 4/1987 | Dwek et al. | 435/18 |
| 4,751,084 | 6/1988 | Feder et al. | 424/94.64 |
| 4,833,085 | 5/1989 | Schaumann et al. | 435/240.27 |
| 4,927,630 | 5/1990 | Feder et al. | 424/94.64 |

FOREIGN PATENT DOCUMENTS

143081 5/1985 European Pat. Off. .

OTHER PUBLICATIONS

Parekh, R. B. et al., *Nature*, 316:452–457, 1985.
Perry, J. H., ed., *Chemical Business Handbook*, McGraw-Hill, New York, 1954, pp. 20-4 through 20-6.
Mohr P. et al., *Affinity Chromatography* vol. 33, Marcel Dekker Inc., New York, 1985, pp. 98, 200, 245.
Giddings, J.C. et al., *Advances in Chromatography*, vol. 29, Marcel Dekker, Inc., New York 1985, 85, 100.
Giddings, J. C. et al., *Advances in Chromatography*, vol. 30, Marcel Dekker, Inc., New York, 1989, pp. 97,105.
Parekh et al., Biochemistry 28, 7644–7662, 7670–7679 (1989).
Wittwer et al., Biochemistry 28, 7662–7669 (1989).
Howard et al., J. Cell. Biol. 107, 584a (1988).
Wittwer et al., J. Cell. Biol. 107, 584a (1988).
Einarsson et al., Biochim. Biophys. Acta. 830, 1–10 (1985).
Fuhrmann et al., Nature 307, 755–758 (1984).
Elbein et al., ARch. Biochem. Biophys. 285, 579–588 (1984).
Gross et al., Eur. J. Biochim. 150, 41–46 (1985).
Bischoff & Kornfeld, Biochem. Biophys. Res. Commun 125, 324–331 (1984).

*Primary Examiner*—Richard A. Schwartz
*Assistant Examiner*—Marianne Porta
*Attorney, Agent, or Firm*—Scott J. Meyer; James W. Williams, Jr.

[57] ABSTRACT

A method of increasing the specific activity of tissue plasminogen activator is disclosed which comprises increasing the proportion of neutral oligosaccharides in the tissue plasminogen activator glycoprotein.

3 Claims, 9 Drawing Sheets

METHOD OF INCREASING SPECIFIC ACTIVITY OF T-PA

BACKGROUND OF THE INVENTION

This invention relates to a method of increasing the specific activity of tissue plasminogen activator (tPA).

Tissue-type plasminogen activator (tPA) is an example of a glycoprotein whose biological properties are a reflection of the cooperative interaction of individual protein domains and the oligosaccharides at specific sites within the protein. The protein has a 527 amino acid sequence comprised of five domains: a fibronectin finger-like domain at the amino terminus, an epidermal growth factor-like domain, two kringle type domains and the serine protease domain at the carboxyl terminus [Pennica et al., Nature 301, 214-221 (1983); Banyai et al., Biochem. Biophys. Res. Commun. 125, 324-331 (1983)]. The serine protease domain catalyzes the conversion of plasminogen to plasmin, and this activity is stimulated by fibrin [Hoylaerts et al., J. Biol. Chem. 257, 2912-2919 (1982); Ranby, Biochem. Biophys. Acta 704, 461-469 (1982)]. Fibrin stimulation is thought to be mediated by binding sites for native fibrin in the fibronectin-like finger domain and for plasmin-degraded fibrin or lysine-like ligands in the second kringle domain [van Zonneveld et al., J. Biol. Chem. 261, 14214-14218 (1986); Verheijen et al., EMBO J. 5, 3525-3530 (1986)]. The function of the growth factor and the first kringle domains are less well established, but both are thought to be involved in the clearance of tPA from the circulation. Deletion of the growth factor domain prolongs the half-like of the tPA [Kalyan et al., J. Biol. Chem. 263, 3971-3978 (1988); Browne et al., Ibid. 263, 1599-1602 (1988)]. In the case of the first kringle domain, clearance appears to be mediated by the high mannose N-linked oligosaccharide side-chain present at Asn-117 within the kringle. Endo H treatment to selectively remove this oligosaccharide or site-directed mutagenesis to eliminate the glycosylation at this position results in a 3 to 5 fold longer circulating half-life [Lau et al., Bio/-Technol. 5, 953-958 (1987); Hotchkiss et al., Thromb. Haem. 60, 255-261 (1988)]. In harmony with this, Kuiper et al., J. Biol. Chem 263, 18220-18224 (1988), found evidence for two separate clearance mechanisms. The liver parenchymal cell clearance of tPA was independent of carbohydrate, whereas tPA recognition by endothelial cells involved the mannose receptor.

In addition to this role in clearance, two observations suggest that both the enzymatic activity of tPA and its affinity for lysine are influenced by glycosylation. First, the type I glycoform (oligosaccharide at Asn-117, -184 and -448) and the type II glycoform (oligosaccharide at Asn-117 and -448 only) have been shown to have significantly different in vitro activities [Einarsson et al., Biochem. Biophys. Acta 830, 1-10 (1985); Wittwer et al., J. Cell Biol. 107, 584a (1988); Wittwer et al., Biochemistry 28, 7662-7669 (1989)]. Second, tPA isolated from different cell types have been shown to have different activities, even though the amino acid sequences are identical. Evidence was presented to support the hypothesis that the activity differences were the result of variations in oligosaccharide structure [Parekh et al., Biochemistry 28, 7644-7662 (1989); Howard et al., J. Cell. Biol. 107, 584a (1988); Wittwer et al., Biochemistry 28, 7662-7669 (1989)]. See also Feder et al., U.S. Pat. No. 4,751,084. Therefore, both the extent and type of oligosaccharide structures on the tPA protein appear to affect enzymatic activity.

BRIEF DESCRIPTION OF THE INVENTION

In accordance with the method of the invention, the specific activity of tPA is increased by substantially increasing the proportion of neutral oligosaccharides relative to other oligosaccharides in the tPA glycoprotein.

In two preferred embodiments of the invention, the proportion of neutral oligosaccharides in the tPA glycoprotein is increased to thereby increase the tPA specific activity by:

1) producing the tPA under in vitro cell culture conditions in the presence of the golgi α-mannosidase I inhibitor, deoxymannojirimycin, whereby a substantial shift is produced in the sugar moieties of the tPA glycoprotein from charged, complex oligosaccharides to high mannose forms, or 2) cleaving the charged sialic acid residues from the tPA oligosaccharides by treatment of the tPA glycoprotein with neuraminidase.

Both of the foregoing embodiments of the invention increased the specific activity of tPA. Production of the tPA in the presence of deoxymannojirimycin (dMM-tPA) increased lysine-Sepharose® affinity and fibrinogen-fragment stimulated activity. The activity was increased as much as two-fold, with the magnitude of increase dependent on cell source. Analysis of the N-linked oligosaccharides from dMM-tPA by gel permeation chromatography on Bio-Gel® P4 resin indicated that a shift had occurred from charged, complex oligosaccharides to high mannose forms. The increased activity and lysine affinity of dMM-tPA were shown to not be a consequence of increased synthesis of type II tPA (decreased glycosylation of site Asn-184).

Although neuraminidase treatment of tPA produced similar increases in specific activity, it did not increase tPA affinity for lysine.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the accompanying drawings in which:

FIGS. 4a–f show the Lysine-Sepharose chromatography of 370 μg CHO-r-tPA (a), 840 μg dMM-CHO-r-tPA (b), 520 μg hcf-tPA (c), 150 μg dMM-hcf-tPA (d), 360 μg mouse C127-r-tPA produced in the presence of butyrate (e), and 100 μg dMM-C127-r-tPA produced in the presence of butyrate (f). For panels a, b, e and f the amidolytic activity of each fraction was measured as described in Examples hereinafter. The full-scale values for these panels are (a) 10 mAU/min, (b) 15 mAU/min, (e) 1.5 mAU/min and (f) 0.4 mAU/min. For panels (c) and (d) a modification of the amidolytic assay was employed in which an endpoint absorbance at 405 nm was read after 16 hr. For panel (c), the y axis scale is 0–600 mAU; for panel (d), the y axis scale is 0–200 mAU.

FIGS. 5a and 5b show the reversed-phase HPLC of tryptic peptides from mouse dMM-C127-r-tPA (a) control C127-r-tPA (b). Only the relevant portion of each chromatogram is shown. The eluate was monitored at 277 nm using a Hewlett-Packard HP 1090A liquid chromatograph with photodiode array detector. The elution position of the peptide containing the glycosylated Asn-117, nonglycosylated Asn-184, and the family of glycopeptides containing glycosylated Asn-184 are indicated by G117, U184, and G184, respectively.

The essential advantages of the invention to increase the specific activity of tPA is illustrated herein with tPA glycoprotein from several different sources, namely normal human colon fibroblast cells (hcf), Chinese hamster ovary cells (CHO), and mouse cells (C-127). These and other such cells for the production of glycosylated tPA are well known. For example, production of tPA by the cell culture of normal hcf cells is described in U.S. Pat. No. 4,751,084. Production of recombinant tPA from CHO cells is illustrated in U.S. Pat. No. 4,766,075 and European Patent Application 117,059, published Aug. 29, 1984. Production of recombinant tPA from mouse C-127 cells is illustrated in European Patent Application 178,105; published Apr. 16, 1986. It will be appreciated, however, that the invention is not limited to any particular source or method of production of the tPA.

The deoxymannojirimycin used in a preferred embodiment of the invention also is known chemically as 1,5-dideoxy-1,5-imino-D-mannitol. Methods for its synthesis are described in U.S. Pat. No. 4,861,892.

The following examples will further illustrate the invention in greater detail although it will be understood that the invention is not limited to these specific examples or the details recited therein.

EXAMPLES

Methods

Source of cells and tPA samples

Recombinant mouse C127 (C127-rtPA) and Chinese hamster ovary CHO (CHO-rtPA) cells containing the tPA cDNA in suitable expression vectors were the same as previously described by Parekh et al., *Biochemistry* 28, 7670–7679 (1989). Human colon fibroblast (hcf) cells (cell line CCD-18Co) were obtained from the American Type Culture Collection, ATCC CRL-1459, and maintained as in previous studies reported by Parekh et al., *Biochemistry* 28, 7644–7662 (1989), and in U.S. Pat. No. 4,751,084. tPA was purified from culture media by affinity chromatography using the *Erythrina caffra* protease inhibitor [Joubert and Dowdle, *Thromb. Haem.* 57, 356–360 (1987)] immobilized on Sepharose ® 4B (Pharmacia) and, in some cases by a second gel filtration step [Parekh, et al., *Biochemistry* 28, 7644–7662 (1989)]. For tests with neuraminidase treatment, Bowes melanoma tPA was obtained from American Diagnostica Inc., hcf-tPA was purified by affinity chromatography as described above, and recombinant tPAs were prepared as described by Parekh et al, *Biochemistry* 28, 7670–7679 (1989). tPA preparations were judged pure by polyacrylamide gel electrophoresis in the presence of sodium dodecyl sulfate (SDS-PAGE), or by high performance analytical gel filtration chromatography.

Metabolic labeling of tPA from recombinant C127 cells (C127-r-tPA)

Cells were incubated in Dulbecco's minimal essential medium (DMEM) containing low glucose (1.5 mg/ml) and 1 mM deoxymannojirimycin (dMM) (Boehringer-Mannheim) for two hours, D-1-[$^3$H]mannose (Amersham) (18 Ci/μmole, 10μ Ci/ml) was added, and incubation continued twenty more hours.

Deoxymannojirimycin treatment of cells

Recombinant CHO cells were grown in DMEM containing 5% calf serum and methotrexate and then incubated with or without 0.6 mM dMM in serum-free DMEM containing dialyzed 0.5% lactalbumin hydrolysate (LAH) (Miles). After 4 hr, dMM containing culture fluid was replaced with fresh serum-free medium containing dMM and LAH, and the incubation continued for 24 hr.

Human colon fibroblast (hcf) cells were grown in medium containing 3 parts DMEM to one part F12 medium, both obtained from Gibco, and buffered with 35 mM Hepes (Sigma) (DFH buffered salts). This was supplemented with 1 mM glutathione, 20 μM ethanolamine, 30 nM sodium selenite, 1×trace elements (all from Sigma), 100 μg/ml bovine serum albumin, and 5 μg/ml iron-saturated transferrin (Miles) (DFH medium), supplemented with 10% fetal calf serum (Hazelton) (Ser-DFH medium). For deoxymannojirimycin treatment, cells were preincubated 2 days either in the above medium or in medium supplemented with 1 mM dMM (Boehringer-Mannheim). For tPA production, cells were first washed with DFH buffered salts and allowed to condition fresh DFH medium, supplemented with 15 ng/ml epidermal growth factor (EGF) (Collaborative Research), 5 μg/ml insulin (Sigma) and Excyte, 1:1000 (Miles) (Sup-DFH medium), with or without dMM. Production continued for 3 weeks with daily removal and replacement of 30–50% of the culture fluid. Inhibitor concentrations up to 15 mM were nontoxic to the cells and no morphological changes were observed.

For the production of mouse C127-r-tPA from recombinant cells in the presence of butyrate (Btr-C127-r-tPA), mouse C127 cells were cultured in the same medium described for the hcf cells, except that the Ser-DFH and the Sup-DFH media also contained 2.5 mM sodium butyrate [Mroczkowski et al., Proc. Natl. Acad. Sci. USA 85, 126–130 (1988)].

Digestion of tPA samples with neuraminidase

Each tPA sample (25 μg/ml) was incubated 16 hrs at room temperature with or without Arthrobacter ureafaciens neuraminidase (Calbiochem) (28 mU/ml) in a buffer containing 140 mM sodium acetate and 280 mM ammonium bicarbonate, pH 5.0.

Lysine-Sepharose chromatography

This was performed as previously described by Parekh et al., Biochemistry 28, 7644–7662 (1989), using a 1.6×92 cm column. Fractions (3 ml) were collected at 0.15 ml/min. The amidolytic activity of each fraction was measured. For tPA metabolically labeled with [$^3$H]mannose, an 150 μl aliquot of each fraction was dissolved in 15 ml Instagel (Packard) and radioactivity was quantitated using a Packard 2200CA liquid scintillation analyzer.

Assays of tPA activity

Direct hydrolysis of S-2322 (H-D-Val-Gly-Arg-p-nitroanilide, KabiVitrum) and activation of plasminogen in the presence of fibrinogen fragment stimulator were measured using the direct amidolytic and stimulated indirect amidolytic assays previously described by Wittwer et al., Biochemistry 28 7662–7669 (1989). Since these assays were performed in 96-well micro-titration plates, 50 μl mineral oil was overlayed on each 100 μl reaction mixture to prevent evaporation during extended incubations. Because of recognized activity differences between single and two-chain tPA in these assays [Ranby et al., FEBS Lett. 146, 289–293 (1982); Boose et al., Biochemistry 28, 635–643 (1989)], samples were treated with plasmin (10 ng/ml, 2 hr) to convert single to two-chain tPA prior to assay [Wittwer et al., Biochemistry 28, 7662–7669 (1989)].

The results of each assay were reported relative to the activity of an equivalent amount of Bowes melanoma-derived tPA (m-tPA) (American Diagnostica, Inc.) having a specific activity of 534 International Units per μg. Protein was determined by a tPA ELISA, using commercial reagents from American Diagnostica, Inc. Thus, assay results were normalized to equivalent levels of tPA antigen.

The percentage of tPA antigen which bound to fibrin during clot formation was determined as previously described by Wittwer et al., Biochemistry 28 7662–7669 (1989) using the general method of Rijken et al., J. Biol. Chem. 257, 2920–2925 (1982). Fibrin binding was also determined in the presence of 10 mM ε-amino-caproic acid to eliminate binding due to the lysine binding site on the tPA second kringle domain. Preliminary studies showed that 10 mM ε-aminocaproic acid completely inhibited the binding of tPA to lysine-Sepharose, an observation consistent with those of others [Cleary et al., Biochemistry 28, 1884–1891 (1989)].

Tryptic digestion of tPA and isolation of glycopeptides

Samples were prepared according to the method of Pohl et al., Biochemistry 23, 3701–3707 (1984), modified as previously described by Parekh et al., Biochemistry 28, 7644–7662 (1989). C127-rtPA (approx. 400 μg of tPA produced in the presence of dMM or 180 μg of control) was reduced, carboxymethylated, digested with trypsin, and subjected to HPLC using a Nucleosil C-18, 5μ, 100 Å, 4.6×250 mm column (Macherey-Nagel, Inc.) at room temperature. A flow-rate of 1 ml/min was maintained during gradient elution from 0% to 40% acetonitrile (0–120 min) and then from 40% to 90% acetonitrile (120–170 min). All HPLC elution solvents contained 0.1% trifluoroacetic acid.

Oligosaccharide purification, radiolabelling and analysis

Ammonium bicarbonate solutions of tPA were lyophilized to dryness. The N-linked carbohydrates were released by treatment with anhydrous hydrazine, followed by N-acetylation and reduction with NaB[$^3$H]$_4$, according to published procedures of Parekh et al., Biochemistry 28, 7644–7662 (1989). Thus, the protein was cryogenically dried over activated charcoal at −196° C. Asparagine-linked oligosaccharides were released by treatment with fresh double-partial vacuum distilled anhydrous hydrazine at 25°–30° C. in sealed glass tubes under dry argon. The temperature of the reaction mixture was raised from 30° C. to 85° C. at 10 degrees C/hr, and then held at 85° C. for 13 hrs. Hydrazine was removed under vacuum at 25° C, followed by repeated co-evaporation with anhydrous toluene. Re-N-acetylation was carried out with a five-fold molar excess of acetic anhydride in saturated NaHCO$_3$ for 10 min at 0° C., and then for 50 min at room temperature. Sodium ions were removed by passage through Dowex ® AG-50×12 resin, and the oligosaccharides were applied to Whatman 3MM paper for descending paper chromatography and developed in 1-butanol/ethanol/water [4:1:1] for 60 hrs at 28° C. The samples were eluted with water and treated with 1 ml of 10 mM cupric acetate to completely remove the acetohydrazide group from the reducing termini of the oligosaccharide. Oligosaccharides were applied to Chelex-100 [Na+ form] over Dowex AG-50×12 [H+ form] resins to remove cupric ions. The sample was reapplied to Whatman 3MM paper for descending paper chromatography. Oligosaccharides recovered within 5 cm from the origin were reduced by treatment with 6 mM NaB[$^3$H$_4$ (10 Ci/mMol, NEN) in 50 mM sodium hydroxide buffered to pH 11.0 with boric acid. After incubation with NaB[$^3$H]$_4$, samples were quenched with excess unlabelled NaBH$_4$. The [$^3$H]-oligosaccharitols were desalted by passage through Dowex AG-50 resin, co-evaporated with acidic methanol to remove borate and purified by descending paper chromatography. [$^3$H]-oligosaccharides were then treated with Arthrobacter ureafaciens neuraminidase (Calbiochem), 50 μl/sample, 10 units/ml in 0.1M sodium acetate, pH 5.0, for 18 hr at 37° C. Release of sialic acid was monitored by paper electrophoresis and ion exchange chromatography, as described above. [$^3$H]-asialo-oligosaccharides were then passed through a column containing a 0.1 ml bed of each of Chelex-100, Dowex AG-50×12 [H+ form], with 0.5 mg of isomalto-oligosaccharides produced by a partial acid hydrolysate of dextran and applied to a Bio-Gel ® P4 column (400 mesh, 1.5 cm×100 cm). The column was maintained at 55° C. in water at a flow rate of 0.2 ml/min. The effluent was monitored by a Raytest radioactive detector (IN/US, Fairfield, N.J., model Ramona D) and a ERMA refractive index monitor (model ERC7510) prior to collection. Analog signals from these instruments were digitized using a Nelson Analytical ADC interface and the digital values were analyzed by computer (model 35741A, Hewlett-Packard). Digestions with *Aspergillus saitoi* $\alpha$1,2-mannosidase and jack bean mannosidase were as follows: 10 mU in 10 $\mu$l of 0.1M sodium acetate, pH 5.0 and 10 mU in 10 $\mu$l of 20 mM citrate, pH 4.5, plus 40 mM zinc acetate, respectively, for 18 hrs at 30° C.

RESULTS

Effect of dMM treatment on enzymatic activity

Recombinant mouse C127 (r-C127) and Chinese hamster ovary CHO (r-CHO) cell lines containing the tPA cDNA in suitable expression vectors, and a normal tissue-derived human colon fibroblast (hcf) cell strain were cultured in the presence or absence of dMM. Additionally, the recombinant C127 cells were sometimes cultured in the presence of butyrate to increase expression levels.

After purification, these tPA preparations were assayed in two different in vitro activity assays. The ability of tPA to activate plasminogen in the presence of fibrinogen fragments was measured by an indirect amidolytic assay. In this assay, the fibrinogen fragments mimic the stimulatory properties of fibrin, and are thought to interact primarily with the lysine-binding site on the second kringle domain [van Eonneveld et al., *J. Biol. Chem.* 261, 14214–14218 (1986); Verheijen, *EMBO J.* 5, 3525–3530 (1986)]. The other assay, the direct amidolytic assay, measures the ability of tPA to hydrolyze a low molecular weight chromogenic peptide substrate. Previous reports of these two assays has shown that the more physiologically relevant indirect amidolytic assay is sensitive to changes in glycosylation, while the direct amidolytic assay shows less variation [Wittwer et al., *Biochemistry* 28, 7662–7669 (1989)]. Such results are also demonstrated by the activities of samples shown in Tables I and II, below. Table I, summarizes the effect of dMM culturing on tPA activity in these two assays. In most cases, dMM-tPA had substantially higher activity in the indirect assay, but had relatively unchanged activity in the direct assay, when compared to control preparations. Both the control specific activity and the magnitude of the increase depended greatly on the cell type used and on the culture conditions. In contrast to tPA from other sources, dMM-hcf-tPA did not show a significant increase in indirect amidolytic activity. In addition, the control specific activity of C127 r-tPA was much higher if produced in the presence of sodium butyrate, which has a stimulatory effect on the metallothionein promoter used in the r-tPA expression vector for these cells [Mroczkowski et al., *Proc. Natl. Acad. Sci. USA* 85, 126–130 (1988)]. Under both culture conditions, however, dMM treatment resulted in large increases in the specific activity over those obtained with untreated samples. Analysis of type I and type II glycoforms, separated by lysine-Sepharose chromatography (see below) indicated that the activities of both glycoforms were increased by dMM.

Oligosaccharide Structure

To determine what effect dMM treatment had on the structure of the tPA oligosaccharides, the purified proteins from recombinant Chinese hamster ovary (CHO), human colon fibroblast (hcf) and recombinant mouse C127 cells were treated with hydrazine to release the N-linked oligosaccharides. The oligosaccharides were purified by paper chromatography, radiolabeled by reduction with [$^3$H]-sodium borohydride and treated with neuraminidase to release sialic acid prior to gel permeation chromatography on Bio-Gel® P4. The Bio-Gel P4 profiles of samples produced in the presence and absence of dMM are shown in FIG. 1. Radiolabeled samples were co-chromatographed with unlabeled isomaltose polymers as internal standards. The detailed structures of the untreated hcf samples have been described previously by Parekh et al., *Biochemistry* 28, 7644–7662, (1989); and U.S. Pat. No. 4,751,084. Complex bi, tri or tetra antennary oligosaccharides elute at values greater than 13.5 glucose units, whereas high mannose type elute between 8.8 and 12.8 glucose units. As shown, dMM treatment resulted in a shift in the hydrodynamic volume of the majority of tPA oligosaccharides produced by each cell type to an elution position primarily characteristic of mannoses$_8$ and mannoses$_9$ oligosaccharides. These are the structures expected if dMM completely inhibited all $\alpha$-mannosidase I activity during synthesis of the protein in the cell. Oligosaccharides which eluted between 8.8 and 12.8 glucose units were sensitive to *Aspergillus saitoi* and jack bean $\alpha$-mannosidases, yielding products that eluted at 5.5 and 7.3 glucose units, respectively, thereby confirming that they were high mannose structures. DMM-tPA oligosaccharides eluting at positions greater than 13.5 glucose units were not sensitive to either $\alpha$-mannosidase, demonstrating that these were complex structures whose formation was not inhibited by dMM. Based upon the relative amounts of complex and high mannose oligosaccharides, dMM treatment of hcf and CHO cells resulted in the formation of tPA with at least 85% high mannose oligosaccharides. For tPA from mouse C127 cells, the amount of high mannose chains was greater than 95%.

Figure 1A:
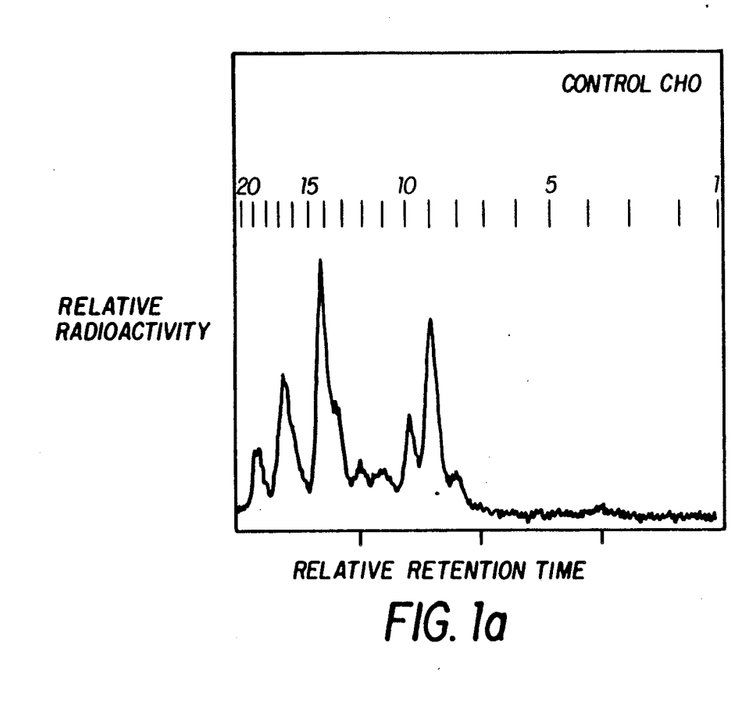
FIGS. 1a-f show the Biogel P4 gel permeation chromatography of oligosaccharides released from various tPAs, namely CHO-rtPA (a,b), hcf-tPA (c,d) and mouse C127-rtPA (e,f), produced in the absence (a,c,e) and presence (b, d, f) of deoxymannojirimycin (dMM), as described in Examples hereinafter.
Figure 1B:
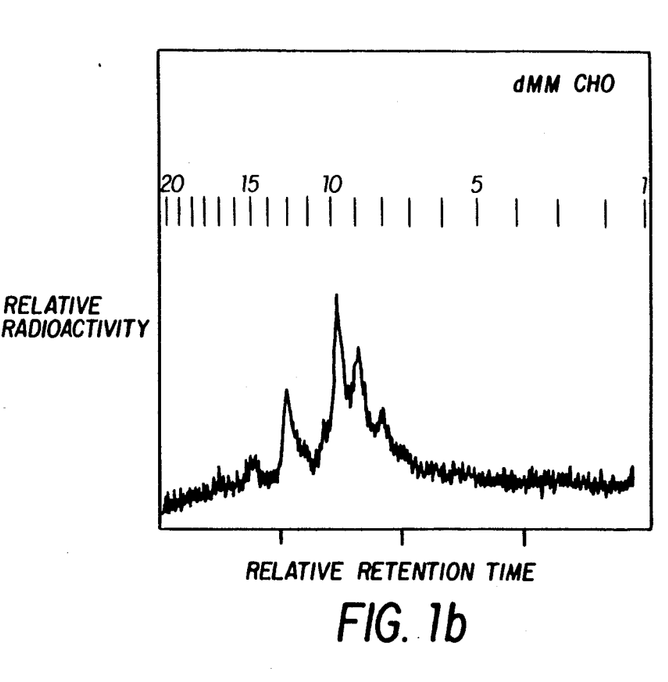
Figure 1C:
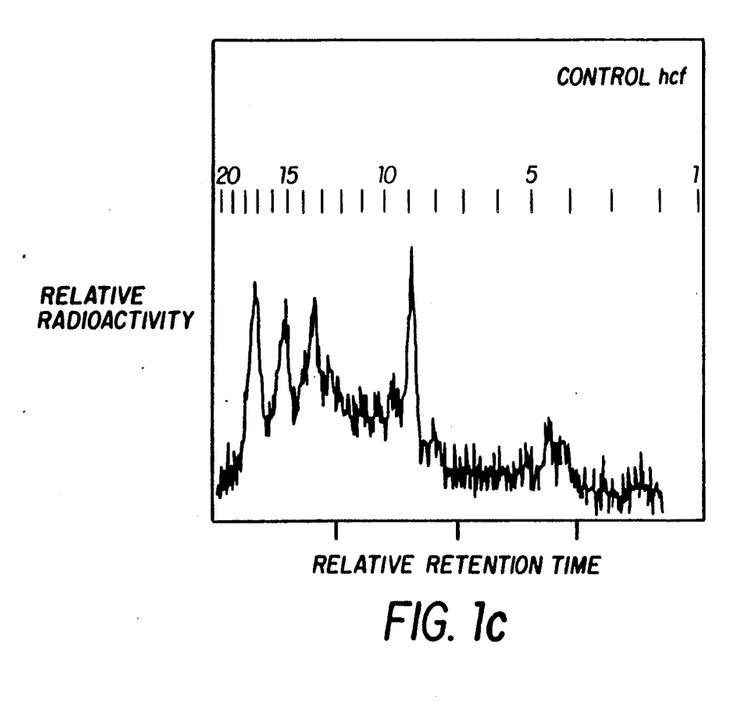
Figure 1D:
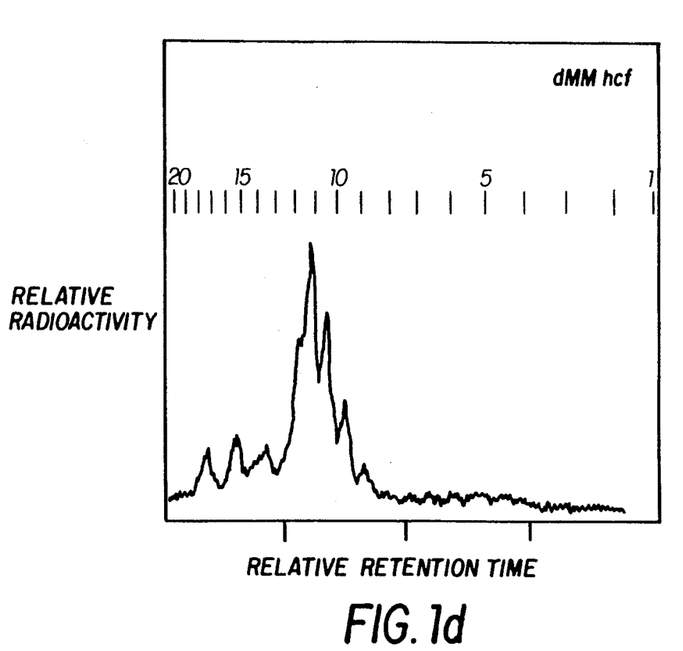
Figure 1E:
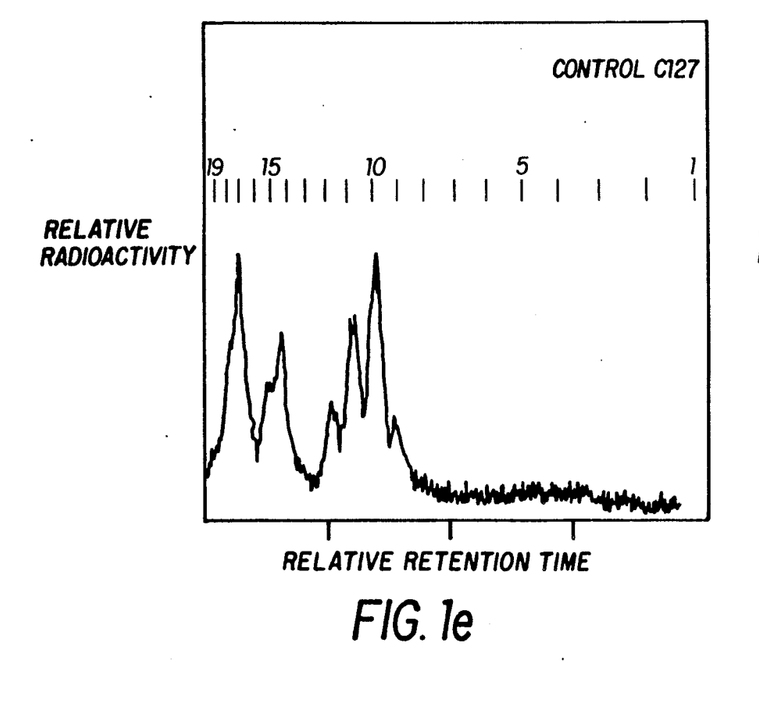
Figure 1F:
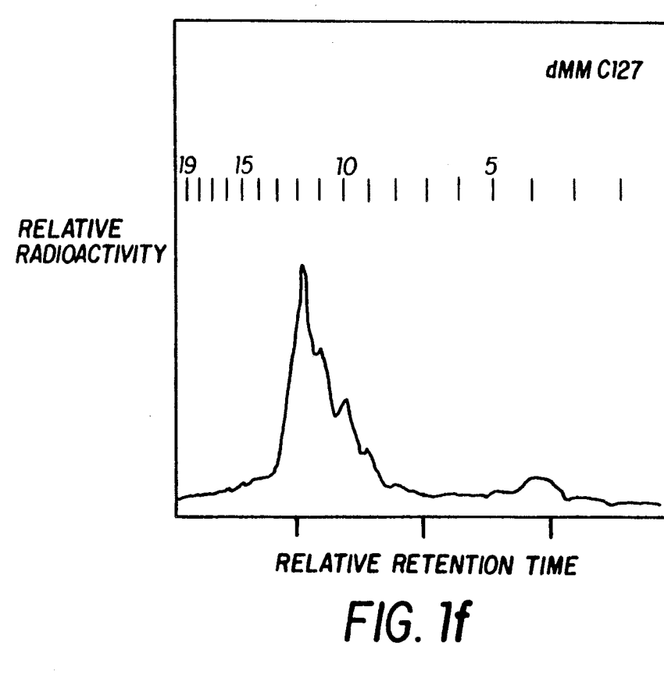
Figure 2A:
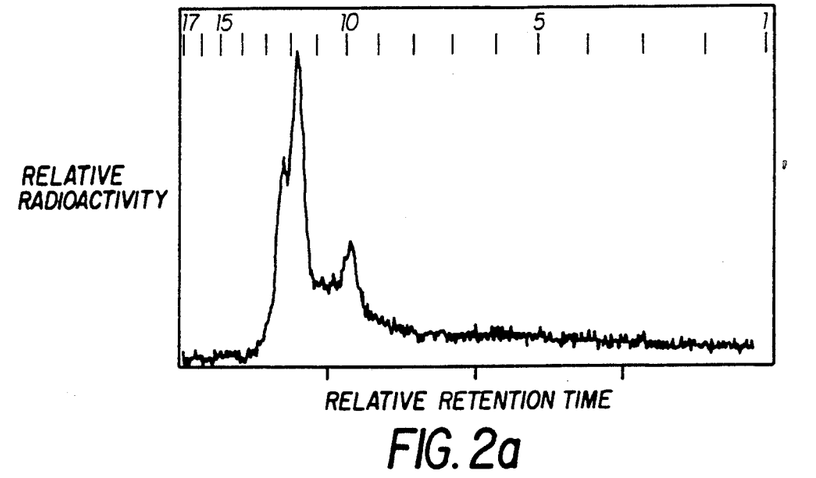
FIGS. 2a-c show the Biogel P4 gel permeation chromatography of oligosaccharides released from each glycosylation site of the C127-rtPA. The glycopeptide fractions corresponding to each glycosylation site were pooled, as previously described by Parekh et al., Biochemistry 28, 7644-7662 (1989), digested with N-glycanase (Genzyme) to release oligosaccharides, digested with neuraminidase (Calbiochem), and chromatographed over the Biogel P4 gel permeation column. The chromatogram obtained for oligosaccharides released from Asn-117 is shown in (a), from Asn-184 in (b), and from Asn-448 in (c).
Figure 2B:
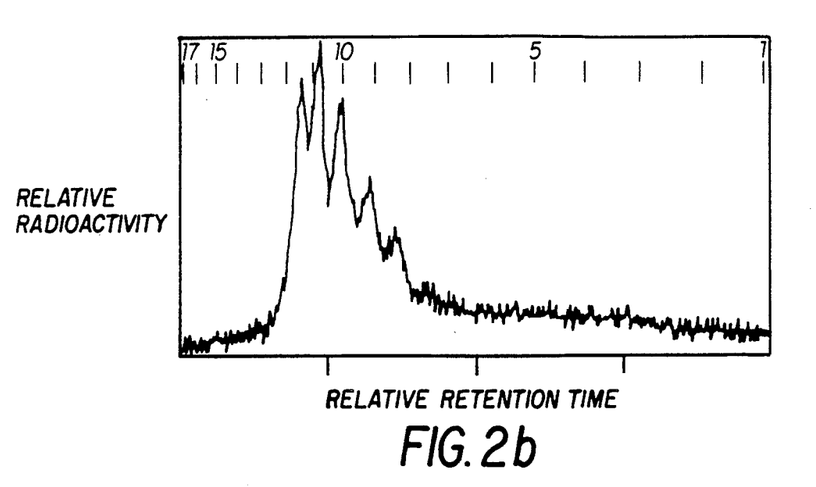
Figure 2C:
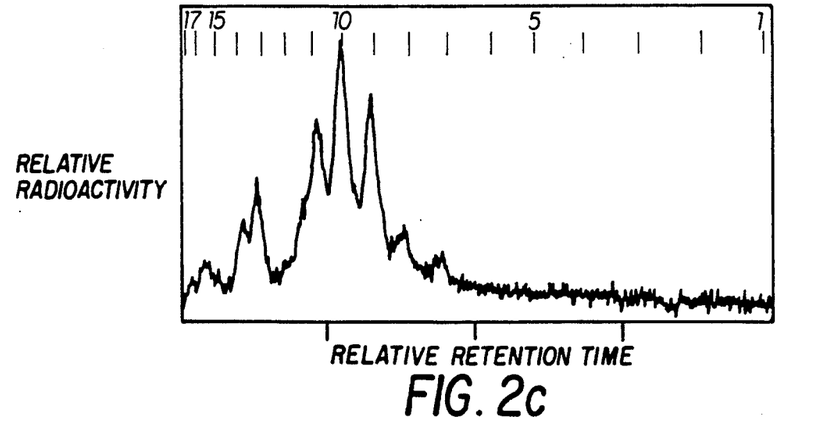

To determine the extent to which dMM treatment was effective in formation of high mannose oligosaccharyl units at Asn-117, -184, and -448, tryptic glycopeptides were isolated from tPA produced in C127 cells in the presence of dMM and the oligosaccharides subjected to Bio-Gel P4 analysis (FIG. 2). These results indicated that inhibition of processing occurred at each glycosylation site, but with different degrees of effectiveness. The effect of dMM was most complete at site 117, in that primarily mannose$_9$ and mannoses$_8$ structures were found. Site Asn-184 oligosaccharide, while completely high mannose in the presence of dMM, was comprised of mannose$_7$, mannose$_6$, and mannose$_5$ species as well as mannose$_9$ and mannoses$_8$, thereby suggesting that some processing of the sugars at this site had occurred. Site Asn-448 contained processed high mannose chains, as well as some complex structures, indicating that the oligosaccharides at this site were not as sensitive to inhibition of $\alpha$-mannosidase.

Affinity for Lysine

Figure 3A:
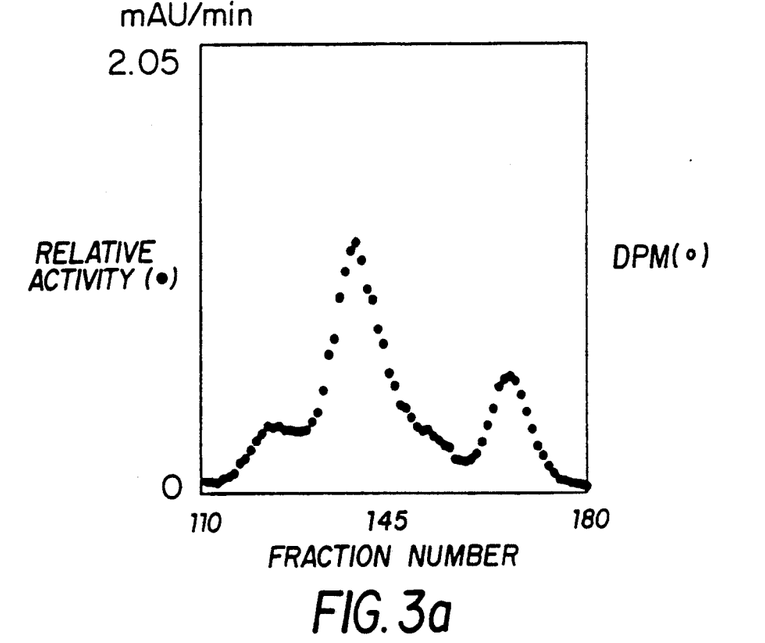
FIGS. 3a and 3b show the Lysine-Sepharose chromatography of 300 μg of control mouse C127-rtPA (a), or of 30 μg of mouse C127-dMM-rtPA (b). For panel (a), the y axis scale is 0–2.05 mAU/min; for panel (b), the left y axis scale is 0–0.46 mAU/min, and the right y axis scale is 0–1028 dpm.
Figure 3B:
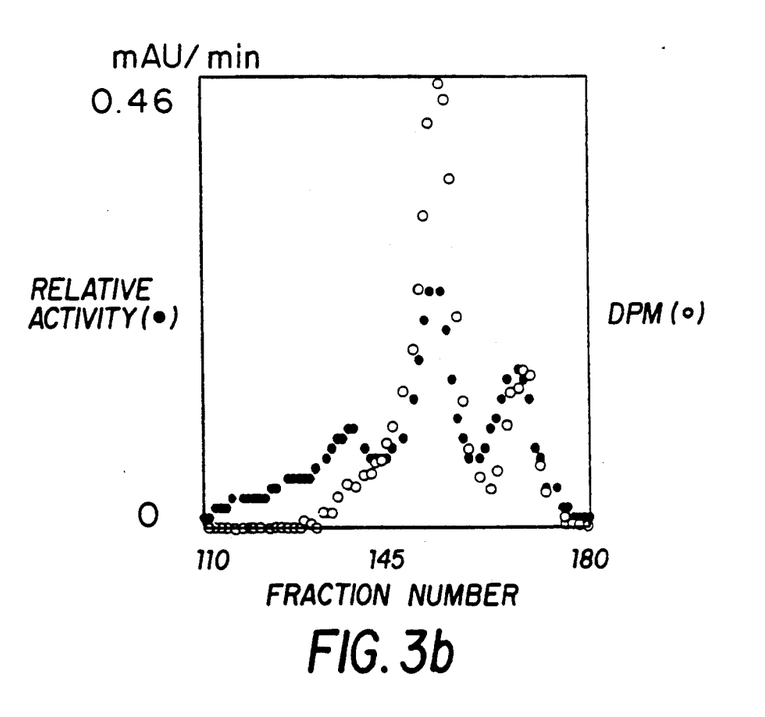
Figure 4A:
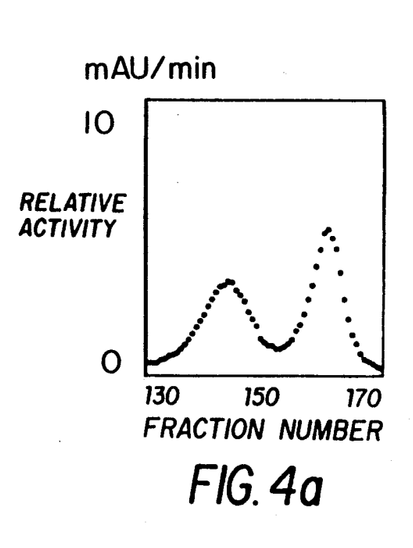
Figure 4B:
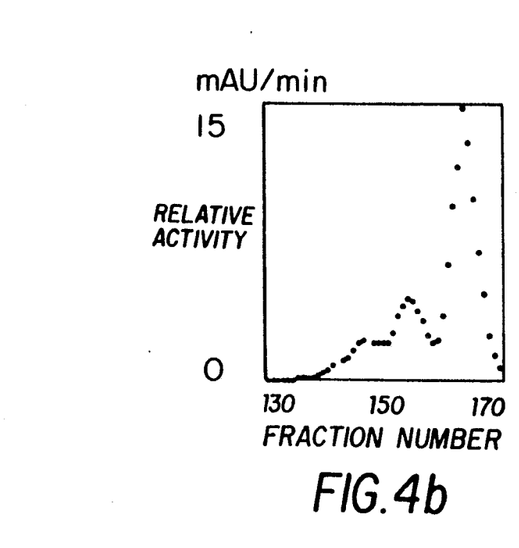
Figure 4C:
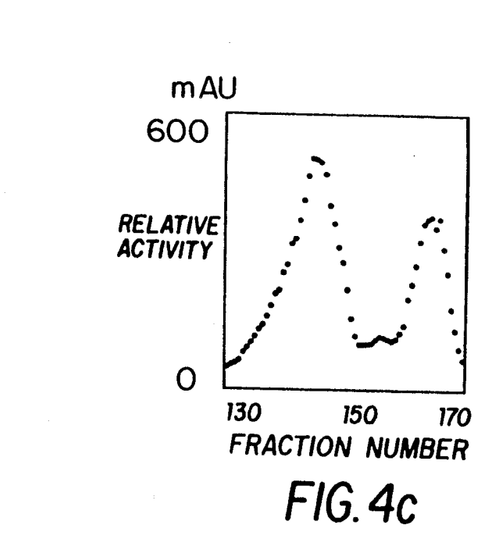
Figure 4D:
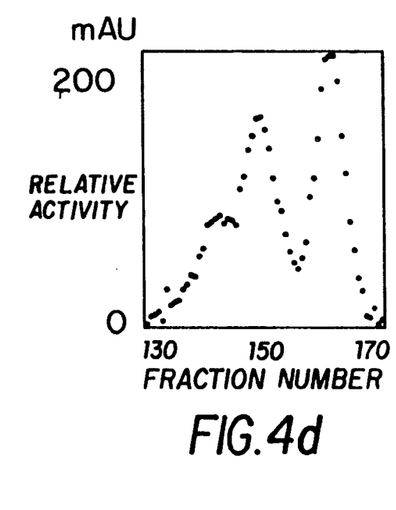
Figure 4E:
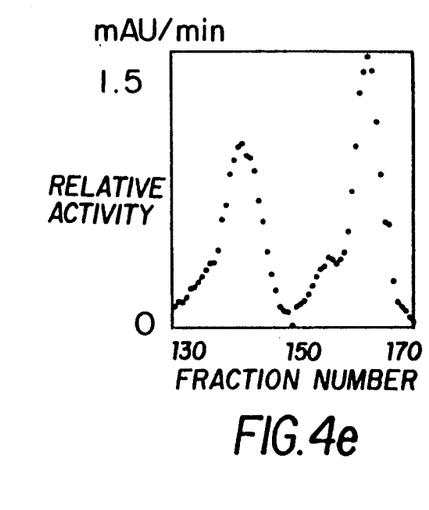
Figure 4F:
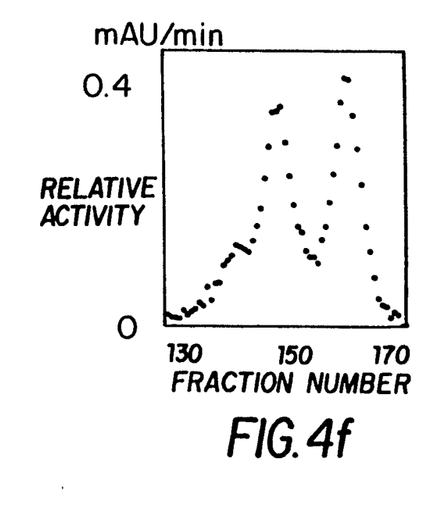

Previous work has shown that type II tPA has higher affinity for lysine-Sepharose and higher specific activity compared to type I tPA when assayed in the presence of fibrinogen fragments. Lysine-Sepharose affinity may, therefore, be a measure of the degree to which tPA activity is stimulated by the binding of fibrinogen peptides containing C-terminal lysine residues. To determine whether elevated activity correlated with an increase in affinity for lysine, tPA from C127 cells was produced in the presence of dMM and labelled with [$^3$H]mannose, added 2 hr after the inhibitor. This was compared to control tPA by chromatography on lysine-Sepharose (FIG. 3). In evaluating these elution profiles, amidolytic activity was used as a rapid measure of protein concentration, since the different tPA glycoforms all have similar amidolytic activities [see Table I and Wittwer et al., *Biochemistry* 28, 7662–7669 (1989). Also, the radioactive label in the dMM-tPA allowed discrimination between tPA synthesized initially and that synthesized after 2 hrs. The elution position of control C127 tPA (FIG. 3A) indicated that the lower affinity (earlier eluting) type I was the predominant species (fractions 130–145) and that there was a smaller amount of the higher affinity type II (fractions 160–173). In the presence of dMM, however, both the radioactivity and the amidolytic activity of lysine-Sepharose fractions indicated the appearance of a higher affinity species eluting intermediate between type I and type II (FIG. 3b). Compared to the amidolytic activity profile, fewer lower affinity tPA species were evident in the radioactive profile, and the species intermediate between type I and type II was even more prominent. The difference between amidolytic activity and radioactivity in FIG. 3b suggests that there was a lag time after the addition of dMM before the inhibitor reached an effective concentration in the cells. It also provides direct evidence that dMM treatment increased the proportion of tPA species with higher lysine-Sepharose affinity. Since greater lysine-Sepharose affinity appears to be correlated with increased activity in the presence of fibrinogen fragments, one reason for the higher activity of dMM-tPA may be increased affinity for this stimulator, as judged by lysine-Sepharose affinity.

To determine whether activity and lysine affinity also correlated for the other cell types employed, the lysine affinity of dMM tPA produced in the CHO, C127 and hcf cells was measured (FIG. 4). As shown, dMM-tPA from all cells had increased lysine affinity. The degree of increase in enzymatic activity appeared to correlate with the extent of increase in lysine-Sepharose affinity. In particular, dMM-hcf-tPA, which showed the smallest increase in specific activity over control (Table I) also showed the smallest increase in lysine-Sepharose affinity (FIG. 4c, d), compared to dMM-tPA from CHO or C127 sources.

Glycosylation of Asn-184

Type I tPA has glycosylation sites Asn-117, -184, and -448 occupied with oligosaccharide, while type II is glycosylated only at Asn-117 and -448. Since type II tPA has a greater affinity for lysine-Sepharose, one possible explanation for the increased affinity of dMM-tPA for lysine is decreased glycosylation at Asn-184. Therefore, the effect of dMM on the proportion of tPA molecules which were glycosylated at Asn-184 was investigated by HPLC tryptic peptide analysis. Previously, the elution positions of the tryptic peptides which contained the oligosaccharides were determined and it was shown that the peptide with an unglycosylated Asn-184, derived solely from type II tPA, eluted at a position that was separate from other peptides [(Parekh et al., *Biochemistry* 28, 7644–7662 (1989)]. The relevant portions of the HPLC tryptic peptide elution profiles for control and dMM-tPA from recombinant C127 cells are compared in FIG. 5. As can be seen, the peak areas of the unglycosylated Asn-184 peptide compared to that of other peptides was very similar in dMM-treated and untreated samples. For example, the area of the peptide containing glycosylation site Asn-117 was 4.03 times greater than the area of the non-glycosylated site Asn-184 peptide from control tPA, and 4.08 times greater than the area of this peptide from dMM-tPA. A direct comparison of glycosylated site Asn-184 peptide with unglycosylated peptide was not possible, since the glycosylated peptide elutes as multiple peaks in the 68–74 min time range, which are not well resolved from other peptides. However, when all the peptide areas in this range were summed, they were 8.47 and 9.19 times the area of the non-glycosylated site Asn-184 peptide from the control and dMM preparations, respectively. The relative areas of the other major peaks in FIG. 3 were all within 10% of each other. These data suggest that dMM does not influence the presence or absence of oligosaccharide at Asn-184, and that the increased affinity for lysine-Sepharose and increased activity of dMM-tPA is not due to a change in the ratio of type II to type I tPAs.

The effect of neuraminidase digestion on enzymatic activity and lysine affinity As a second means to demonstrate the influence of oligosaccharide composition on activity, terminal sialic acid residues were removed from tPA preparations using neuraminidase from *Arthrobacter ureafaciens* [Uchida et al., *J. Biochem.* 86, 1573–1585, (1979)], an enzyme that cleaves both the α-2,3 and the α-2,6 sialic acid linkages. tPA from Bowes melanoma, r-C127, r-CHO and human colon fibroblast cells were tested. The results are summarized in Table II. Neuraminidase treatment did not significantly increase direct amidolytic activity for any of the tPAs. Rather, direct amidolytic activity was either unchanged or showed a small (up to 30%) decrease. This is consistent with previous findings [Table I and Wittwer, et al., *Biochemistry* 28, 7662–7669 (1989)] which demonstrate that oligosaccharide variation has little effect on the hydrolysis of a low molecular weight peptide substrate, as measured by the direct assay. However, activation of plasminogen in the presence of fibrinogen fragments, as measured by the indirect amidolytic assay, increased 52%, 86% and 100% for r-tPA from C127, CHO, and hcf-tPA, respectively. The most dramatic increase in stimulated amidolytic activity upon neuraminidase digestion was the 4.6-fold increase observed for the earliest eluting fractions of the hcf-tPA type I peak, which sometimes elute as a shoulder preceding the major type I glycoform upon lysine-Sepharose chromatography and have lowered activity [Parekh et al., *Biochemistry* 28, 7644–7662 (1989); Howard et al., *J. Cell. Biol.* 107, 584a (1988)]. The increase was only 14% for m-tPA.

Figure 6:
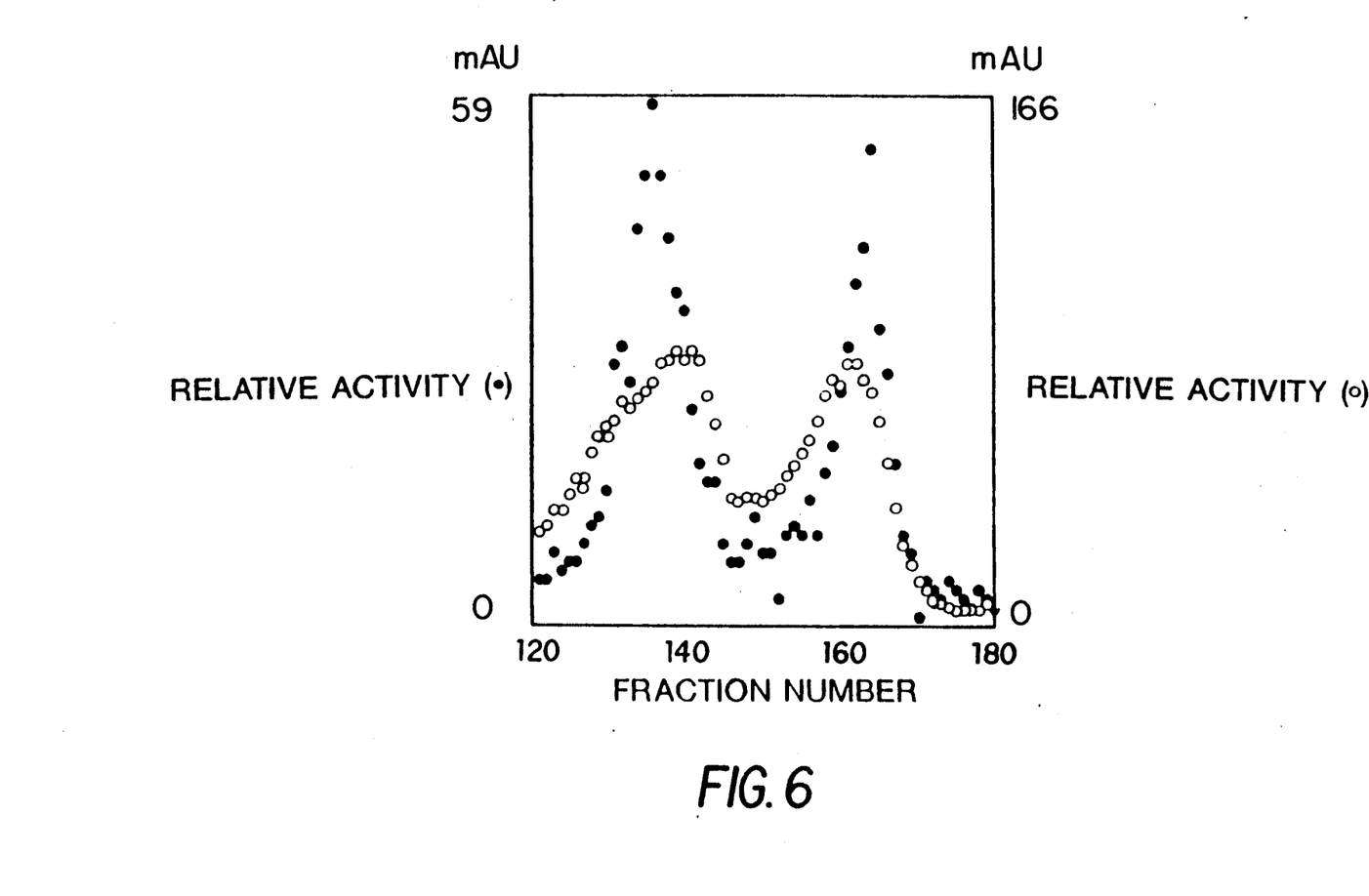
FIG. 6 shows the lysine-Sepharose chromatography of 7.5 μg of either control C127-r-tPA (O) or C127-r-tPA following a 16 hr digestion with *Arthrobacter ureafaciens* neuraminidase (●). The left y axis scale is from 0–59 mAU, and the right y axis scale is from 0–166 mAU. This test was monitored using the direct amidolytic assay described in Examples hereinafter, except the endpoint absorbance following a one day incubation at room temperature was plotted.

In contrast to results obtained with dMM, neuraminidase treatment of C127-tPA did not produce a clear-cut increase in affinity for lysine, but did produce a more heterogeneous lysine-Sepharose profile (FIG. 6). New species with lysine-Sepharose affinity intermediate between that of type I and type II tPA were observed; however, species with lower lysine-Sepharose affinity were also observed. Incomplete digestion with neuraminidase may be an explanation for the heterogeneity.

However, this extent of neuraminidase treatment was sufficient to cause a large increase in activity. The absence of an increase in the overall lysine-Sepharose affinity of neuraminidase-treated tPA suggests that an increase in affinity of the lysine-binding site on tPA kringle 2 is not the reason for the increased activity tPA antigen bound to a forming fibrin clot was essentially unchanged in dMM-or neuraminidase-treated tPA compared to controls. Thus, increased fibrin binding does not appear to be responsible for or correlate with the increased activity of dMM-tPA or neuraminidase-treated tPA.

TABLE I

Specific activity of tPA produced in the presence and absence of deoxymannojirimycin (dMM)[a]

| | Assay | | | | | |
|---|---|---|---|---|---|---|
| | Stimulated Indirect Amidolytic | | | Direct Amidolytic | | |
| tPA Sample | no dMM | + dMM | Ratio[b] | no dMM | + dMM | Ratio[b] |
| | (IU/µg, mean ± SEM) | | | (Relative units, mean ± SEM) | | |
| CHO-r-tPA | 441 ± 36 | 696 ± 43 | 1.58** | 2.02 ± 0.22 | 1.35 ± 0.14 | 0.67* |
| hcf-tPA | 398 ± 15 | 432 ± 21 | 1.09 | 1.02 ± 0.03 | 1.08 ± 0.04 | 1.06 |
| Btr-C127-r-tPA[c] | 549 ± 14 | 820 ± 29 | 1.49** | 1.13 ± 0.01 | 1.20 ± 0.03 | 1.06* |
| C127-r-tPA[d], total | 299 ± 22 | 534 ± 23 | 1.78** | 1.15 ± 0.03 | 1.22 ± 0.03 | 1.06 |
| C127, Type I | 161 ± 3 | 337 ± 11 | 2.08** | 1.10 ± 0.02 | 1.17 ± 0.03 | 1.06 |
| C127, Intermediate | n.p. | 424 ± 22 | 2.63** | n.p. | 1.04 ± 0.03 | 0.95 |
| C127, Type II | 598 ± 20 | 817 ± 23 | 1.33** | 1.01 ± 0.02 | 1.12 ± 0.03 | 1.11* |

[a]See Materials and Methods for test details.
[b]Activity of dMM-tPA divided by activity of tPA produced without dMM. For the C127-r-tPA intermediate species, activity of dMM-tPA was divided by activity of C127-r-tPA type I, since the intermediate is not present in the control sample. Ratios calculated from means which are significantly different at the 95% (*) and 99% (**) level of confidence are so indicated. A student's two-tailed t test was used.
[c]C127-r-tPA produced from cells cultured in the presence of butyrate.
[d]See FIG. 4. "Type I" refers to fractions 129-143, "Intermediate" refers to the species which elutes between type I and type II in dMM-tPA (fractions 147-155), and type II refers to fractions 162-172. The intermediate species is not present (n.p.) in control tPA.

TABLE II

Specific activity of tPA incubated with or without neuraminidase[a].

Figure 5A:
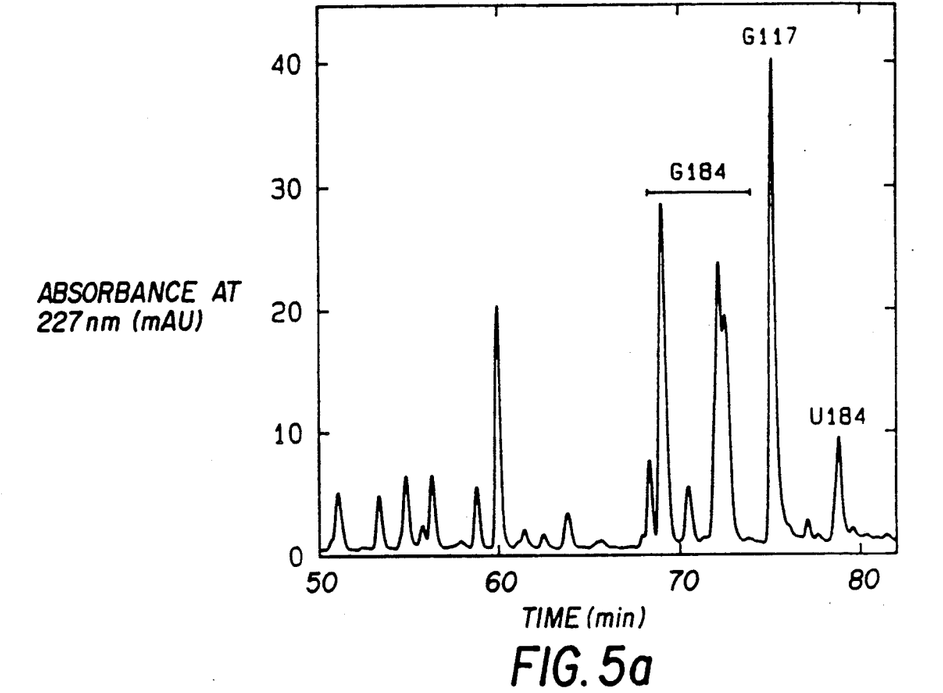
Figure 5B:
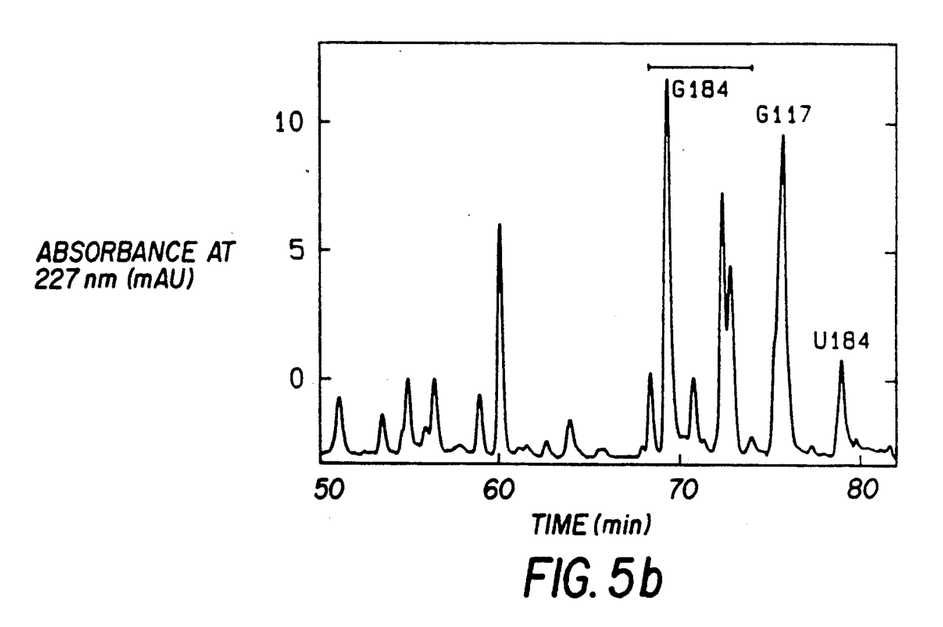

| | Assay | | | | | |
|---|---|---|---|---|---|---|
| | Stimulated Indirect Amidolytic | | | Direct Amidolytic | | |
| tPA Sample | no NA | + NA | Ratio[b] | no NA | + NA | Ratio[b] |
| | (IU/µg, mean ± SEM) | | | (Relative units, mean ± SEM) | | |
| CHO-r-tPA | 439 ± 28 | 665 ± 46 | 1.52** | 1.98 ± 0.12 | 1.92 ± 0.03 | 0.97* |
| hcf-tPA, total | 270 ± 5 | 583 ± 10 | 2.16** | 0.97 ± 0.04 | 0.71 ± 0.01 | 0.73** |
| hcf-tPA, pre-I | 41 ± 5 | 190 ± 9 | 4.63** | 0.86 ± 0.07 | 0.89 ± 0.05 | 1.03 |
| hcf-tPA, type I | 211 ± ±0 | 450 ± 23 | 2.13** | 1.11 ± 0.08 | 0.75 ± 0.01 | 0.68** |
| hcf-tPA, type II | 559 ± 24 | 916 ± 64 | 1.64** | 1.36 ± 0.10 | 0.94 ± 0.04 | 0.69** |
| C127-r-tPA | 306 ± 16 | 529 ± 29 | 1.86** | 1.23 ± 0.07 | 1.20 ± 0.06 | 0.98 |
| m-tPA | 527 ± 32 | 599 ± 52 | 1.14 | 1.13 ± 0.08 | 1.19 ± 0.07 | 1.05 | m-tPA means melanoma tPA
[a]See Materials and Methods for test details.
[b]Activity of NA-treated tPA divided by activity of control tPA. Ratios calculated from means which are significantly different at the 99% (**) level of confidence are so indicated. A student's two-tailed t test was used.
[c]"Pre-I" refers to fractions eluting on the leading edge of type I (similar to fractions 120-135 in FIG. 5c) on lysine-Sepharose; types I and II refer to the central portions of the major peaks.

seen.

Fibrin binding of neuraminidase-treated and dMM-tPA

In addition to the lysine binding site on the second kringle, binding to native fibrin is also thought to involve the finger domain of tPA [van Zonneveld et al., *J. Biol. Chem.* 261, 14214-14218 (1986)]. Although the increase in activity of dMM-tPA appeared to correlate with increased affinity for lysine-Sepharose, some increases in activity occurred without such an increase in lysine affinity (see for example the C127 type II tPA in Table I). Also, neuraminidase treatment increased tPA activity without an overall increase in lysine affinity. This suggested that factors in addition to lysine affinity were important in the activity increases observed. Therefore, the effect of dMM or neuraminidase treatment on fibrin binding was determined both in the presence of 10 mM ε-aminocaproic acid and in its absence. Inclusion of ε-aminocaproic acid in this assay blocks any binding to fibrin mediated by the kringle 2 lysine-binding site, and should allow an assessment of the affinity of other binding sites or domains, presumably the finger region. As shown in Table III, the percentage

TABLE III

Effect of Deoxymannojirimycin or Neuraminidase Treatment on tPA Binding to Clotted Fibin(ogen)

| | % Bound to Clot | | | |
|---|---|---|---|---|
| | (Glycine) | | (EACA) | |
| tPA Sample | mean | SEM | mean | SEM |
| CHO (−) | 75.5 | 1.2 | 35.6 | 2.3 |
| CHO (neur) | 78.6 | 1.2 | 45.0 | 2.0 |
| hcf (−) | 66.2 | 0.6 | 37.2 | 2.6 |
| hcf (neur) | 71.1 | 2.7 | 45.4 | 1.2 |
| hcf (−) | 74.8 | 0.6 | 38.0 | 1.8 |
| hcf (dMM) | 77.7 | 1.0 | 42.4 | 1.4 |
| C127 (−) | 72.6 | 1.5 | 47.9 | 2.0 |
| C127 (neur) | 65.7 | 0.5 | 43.0 | 1.4 |
| C127Bt (−) | 78.6 | 0.5 | 56.3 | 1.8 |
| C127Bt (dMM) | 81.6 | 0.6 | 58.3 | 0.9 |
| Mel (−) | 79.0 | 0.6 | 53.4 | 2.2 |
| Mel (neur) | 78.4 | 0.7 | 57.5 | 2.0 |

Mel means melanoma
EACA means E-aminocapraic acid

Various other examples will be apparent to the person skilled in the art after reading the present disclosure without departing from the spirit and scope of the invention. It is intended that all such other examples be included within the scope of the appended claims.

What is claimed is:

1. The method of increasing the specific activity of human tissue plasminogen activator glycoprotein as evaluated by a stimulated indirect amidolytic assay which comprises increasing the proportion of neutral oligosaccharides relative to other oligosaccharides in said tissue plasminogen activator glycoprotein by producing said tissue plasminogen activator glycoprotein under in vitro mammalian cell culture conditions in the presence of deoxymannojirimycin.

2. The method of increasing the specific activity of human tissue plasminogen activator glycoproteins evaluated by a stimulated indirect amidolytic assay which comprises increasing the proportion of neutral oligosaccharides relative to other oligosaccharides in said tissue plasminogen activator glycoprotein by producing said tissue plasminogen activator glycoprotein under in vitro mammalian cell culture conditions and then cleaving sialic acid residues from the tissue plasminogen activator glycoprotein by treatment with neuraminidase.

3. The method of claim 2 in which the tissue plasminogen activator is derived from the culture of normal human colon fibroblast cells.